US010268485B2

(12) United States Patent
Rasband et al.

(10) Patent No.: US 10,268,485 B2
(45) Date of Patent: *Apr. 23, 2019

(54) CONSTRAINED DEVICE AND SUPPORTING OPERATING SYSTEM

(71) Applicant: TYCO FIRE & SECURITY GMBH, Neuhausen am Rheinfall (CH)

(72) Inventors: Paul B. Rasband, Fremont, CA (US); Vincent J. Lipsio, Jr., Gainesville, FL (US)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 386 days.

This patent is subject to a terminal disclaimer.

(21) Appl. No.: 14/463,754

(22) Filed: Aug. 20, 2014

(65) Prior Publication Data
US 2015/0248297 A1    Sep. 3, 2015

Related U.S. Application Data

(60) Provisional application No. 61/973,962, filed on Apr. 2, 2014, provisional application No. 61/946,054, filed on Feb. 28, 2014.

(51) Int. Cl.
*G06F 9/44* (2018.01)
*G06F 9/4401* (2018.01)
(Continued)

(52) U.S. Cl.
CPC ............ *G06F 9/4416* (2013.01); *A61B 17/00* (2013.01); *G01S 5/02* (2013.01); *G01S 5/0236* (2013.01);
(Continued)

(58) Field of Classification Search
CPC ................................. G06F 8/63; G06F 9/4416
See application file for complete search history.

(56) References Cited

U.S. PATENT DOCUMENTS

| 5,414,812 A | 5/1995 | Filip et al. |
| 6,112,237 A | 8/2000 | Donaldson et al. |

(Continued)

FOREIGN PATENT DOCUMENTS

| CN | 1217078 A | 5/1999 |
| CN | 1672060 A | 9/2005 |

(Continued)

OTHER PUBLICATIONS

Chen et al. "Enix: a lightweight dynamic operating system for tightly constrained wireless sensor platforms." Proceedings of the 8th ACM Conference on Embedded Networked Sensor Systems. Nov. 3, 2010 (http://sensys.acm.org/2010/Papers/p183-Chen.pdf).

(Continued)

*Primary Examiner* — Zahid Choudhury
(74) *Attorney, Agent, or Firm* — Foley & Lardner LLP

(57) ABSTRACT

A networked system for managing a physical intrusion detection/alarm includes an upper tier of server devices, comprising: processor devices and memory in communication with the processor devices, a middle tier of gateway devices that are in communication with upper tier servers, and a lower level tier of devices that comprise fully functional nodes with at least some of the functional nodes including an application layer that execute routines to provide node functions, and a device to manage the lower tier of devices, the device instantiating a program manager that executes a state machine to control the application layer in each of the at least some of the functional nodes.

17 Claims, 11 Drawing Sheets

(51) Int. Cl.

| | | |
|---|---|---|
| *H04L 12/46* | (2006.01) | |
| *H04N 5/76* | (2006.01) | |
| *H04W 16/26* | (2009.01) | |
| *H04L 12/64* | (2006.01) | |
| *H04L 29/08* | (2006.01) | |
| *H04L 29/12* | (2006.01) | |
| *A61B 17/00* | (2006.01) | |
| *G01S 5/02* | (2010.01) | |
| *G01S 13/76* | (2006.01) | |
| *G08B 25/00* | (2006.01) | |
| *H04L 9/00* | (2006.01) | |
| *H04W 8/26* | (2009.01) | |
| *G01S 13/87* | (2006.01) | |
| *G08B 29/18* | (2006.01) | |
| *H04W 88/04* | (2009.01) | |
| *G08B 13/196* | (2006.01) | |
| *H04W 4/38* | (2018.01) | |
| *H04W 92/02* | (2009.01) | |
| *H04L 12/26* | (2006.01) | |
| *H04W 4/00* | (2018.01) | |
| *H04W 84/18* | (2009.01) | |

(52) U.S. Cl.
CPC .......... *G01S 5/0284* (2013.01); *G01S 13/765* (2013.01); *G01S 13/876* (2013.01); *G08B 13/19634* (2013.01); *G08B 25/009* (2013.01); *G08B 29/181* (2013.01); *G08B 29/188* (2013.01); *H04L 9/004* (2013.01); *H04L 12/4625* (2013.01); *H04L 12/6418* (2013.01); *H04L 61/106* (2013.01); *H04L 67/104* (2013.01); *H04L 67/12* (2013.01); *H04L 67/34* (2013.01); *H04N 5/76* (2013.01); *H04W 8/26* (2013.01); *H04W 16/26* (2013.01); *H04W 88/04* (2013.01); *G08B 13/19608* (2013.01); *G08B 25/007* (2013.01); *H04L 43/0805* (2013.01); *H04L 61/6013* (2013.01); *H04L 61/6072* (2013.01); *H04L 67/1051* (2013.01); *H04L 67/1093* (2013.01); *H04W 4/006* (2013.01); *H04W 4/38* (2018.02); *H04W 84/18* (2013.01); *H04W 92/02* (2013.01); *Y04S 40/168* (2013.01)

(56) References Cited

U.S. PATENT DOCUMENTS

| | | | |
|---|---|---|---|
| 6,272,621 B1 | 8/2001 | Key et al. | |
| 6,658,234 B1 | 12/2003 | Dogan et al. | |
| 6,771,385 B1 | 8/2004 | Lizuka et al. | |
| 6,873,260 B2 | 3/2005 | Lancos et al. | |
| 6,888,459 B2 | 5/2005 | Stilp | |
| 7,017,171 B1 | 3/2006 | Horlander et al. | |
| 7,176,808 B1 | 2/2007 | Broad et al. | |
| 7,688,808 B2 | 3/2010 | Ren et al. | |
| 7,908,020 B2 | 3/2011 | Pieronek | |
| 7,966,660 B2 | 6/2011 | Yermal et al. | |
| 8,260,893 B1 | 9/2012 | Bandhole et al. | |
| 8,305,196 B2 | 11/2012 | Kennedy et al. | |
| 8,400,268 B1 | 3/2013 | Malik | |
| 8,527,640 B2 | 10/2013 | Verma et al. | |
| 8,559,344 B2 | 10/2013 | Abusch-Madger et al. | |
| 8,572,290 B1 | 10/2013 | Mukhopadhyay et al. | |
| 8,578,153 B2 | 11/2013 | Johansson et al. | |
| 8,739,176 B1* | 5/2014 | Darling | G06F 9/4881 718/103 |
| 9,037,152 B1* | 5/2015 | Herrera | H04W 64/00 370/338 |
| 2002/0057204 A1 | 5/2002 | Bligh | |
| 2003/0187612 A1* | 10/2003 | Miyake | G06F 9/4806 702/176 |
| 2004/0027243 A1 | 2/2004 | Carrender | |
| 2004/0090329 A1 | 5/2004 | Hitt | |
| 2004/0109059 A1 | 10/2004 | Kawakita | |
| 2005/0052281 A1 | 3/2005 | Bann | |
| 2005/0143133 A1 | 6/2005 | Bridgelall | |
| 2006/0022816 A1 | 2/2006 | Yukawa | |
| 2006/0039356 A1 | 2/2006 | Rao et al. | |
| 2007/0011683 A1* | 1/2007 | Helander | G06F 9/4887 718/104 |
| 2007/0058634 A1 | 3/2007 | Gupta et al. | |
| 2007/0112943 A1 | 5/2007 | Fisher et al. | |
| 2007/0130589 A1 | 7/2007 | Davis et al. | |
| 2007/0186106 A1 | 8/2007 | Ting et al. | |
| 2007/0223451 A1 | 9/2007 | Ren et al. | |
| 2007/0248065 A1 | 10/2007 | Banerjea et al. | |
| 2007/0239350 A1 | 11/2007 | Zumsteg et al. | |
| 2008/0002599 A1 | 3/2008 | Yau et al. | |
| 2008/0056261 A1 | 3/2008 | Osborn | |
| 2008/0068267 A1 | 3/2008 | Huseth | |
| 2008/0144587 A1 | 6/2008 | Gupta et al. | |
| 2008/0204267 A1 | 8/2008 | Luterotti et al. | |
| 2008/0291017 A1 | 11/2008 | Yermal et al. | |
| 2009/0021634 A1 | 1/2009 | Chang | |
| 2009/0222921 A1 | 3/2009 | Mukhopadhyay et al. | |
| 2010/0019901 A1 | 1/2010 | Tsai | |
| 2010/0226342 A1 | 9/2010 | Coiling et al. | |
| 2010/0061272 A1 | 11/2010 | Veillette | |
| 2011/0051656 A1 | 3/2011 | Hethuin et al. | |
| 2011/0310791 A1 | 12/2011 | Prakash et al. | |
| 2012/0039235 A1 | 2/2012 | Chen et al. | |
| 2012/0092183 A1 | 4/2012 | Corbett et al. | |
| 2012/0082062 A1 | 5/2012 | McCormack | |
| 2012/0124367 A1 | 5/2012 | Ota et al. | |
| 2012/0197986 A1 | 8/2012 | Chen et al. | |
| 2013/0055282 A1* | 2/2013 | Yi | G06F 9/4881 718/104 |
| 2013/0003645 A1 | 3/2013 | Shapira et al. | |
| 2013/0064233 A1 | 3/2013 | Hethuin et al. | |
| 2013/0086195 A1 | 4/2013 | Hiniker | |
| 2013/0239192 A1 | 9/2013 | Linga et al. | |
| 2013/0336230 A1 | 12/2013 | Zou et al. | |
| 2014/0052832 A1 | 2/2014 | Dina et al. | |
| 2014/0222892 A1 | 8/2014 | Lee et al. | |

FOREIGN PATENT DOCUMENTS

| | | |
|---|---|---|
| CN | 1871782 A | 11/2006 |
| CN | 101764759 A | 6/2010 |
| CN | 101951341 A | 1/2011 |
| CN | 102035738 A | 4/2011 |
| CN | 103170071 A | 6/2013 |
| CN | 203057531 | 7/2013 |
| EP | 1 885 039 | 2/2008 |
| WO | WO01/06401 | 1/2001 |
| WO | WO2004/068855 | 8/2004 |
| WO | WO2013/159217 | 10/2013 |

OTHER PUBLICATIONS

International Search Report and Written Opinion, PCT/US2015/017251.
International Search Report and Written Opinion, PCT/US15/17680.
U.S. Appl. No. 14/603,602 entitled "Constrained Device and Supporting Operating System".
International Search Report and Written Opinion, PCT/US15/17470.
International Search Report and Written Opinion, PCT/US15/17481.
International Search Report and Written Opinion, PCT/US2012/017477.
International Search Report and Written Opinion, PCT/US15/17688.
International Search Report and Written Opinion, PCT/US15/17696.
International Search Report and Written Opinion, PCT/US15/17931.

(56) References Cited

OTHER PUBLICATIONS

International Search Report and Written Opinion, PCT/US15/17702.

Ying Zhou et al., "*Mobile Agent-based Policy Management for Wireless Sensor Networks*,", Wireless Communications, Networking and Mobile Computing, 2005, Proceedings 2005 Int'l Conference on Wuhan, China, vol. 2, (Sep. 23, 2005), pp. 1207-1210.

European Search Report, PCT/US2015/017212.

Enabling direct connectivity between heterogeneous objects in the internet of things through a network-service-oriented architecture, Aug. 15, 2011, https://jwcn-eurasipjournals.springeropen.com/articles/10.1186/1687-1499-2011-61.

European Search Report, PCT/US2015/017221.

European Search Report, PCT/US2015/017696.

European Search Report, PCT/US2015/017702.

Office Action on Chinese Patent Application No. 201580013946.4 dated Jul. 31, 2018. 1 page.

Office Action on Chinese Patent Application No. 201580016948.9 dated May 30, 2018. 1 page.

Office Action on Chinese Patent Application No. 201580019697 dated May 17, 2018. 1 page.

Office Action on U.S. Appl. No. 14/463,970 dated Jun. 7, 2018. 17 pages.

Office Action on U.S. Appl. No. 14/463,920 dated Jun. 27, 2018. 8 pages.

Office Action on U.S. Appl. No. 14/603,602 dated Jul. 3, 2018. 7 pages.

Office Action on U.S. Appl. No. 15/366,036 dated May 31, 2018. 5 pages.

Office Action on U.S. Appl. No. 15/402,423 dated Jul. 26, 2018. 11 pages.

Office Action on U.S. Appl. No. 15/843,124 dated May 30, 2018. 9 pages.

Cheng, Research on AODV Routing Protocol of Wireless Network, Chinese Master's Theses Full-Text Database, Information Technology Division, Jul. 15, 2007, 79 pages.

First Office Action for Chinese Application No. 201580015282.5, dated Sep. 4, 2018, 18 pages.

Office Action for U.S. Appl. No. 15/402,423, dated Jul. 26, 2018, 10 pages.

Chinese Office Action dated May 30, 2018 in corresponding application No. 201580016948.9.

Office Action for Chinese Application No. 201580013946.4, dated Jul. 31, 2018, 15 pages.

Bhatti et al., Mantis OS: An Embedded Multithreaded Operating System for Wireless Micro Sensor Platforms, Aug. 1, 200, 15 pages.

Office Action for U.S. Appl. No. 14/464,091, dated Sep. 7, 2018, 16 pages.

Notice of Allowance for U.S. Appl. No. 14/603,602, dated Nov. 23, 2018, 8 pages.

Examination Report for European Application No. 15754691.2, dated Sep. 12, 2018, 7 pages.

\* cited by examiner

CONSTRAINED DEVICE AND SUPPORTING OPERATING SYSTEM

CLAIM OF PRIORITY

This application claims priority under 35 U.S.C. § 119(e) to provisional U.S. Patent Application 61/973,962, filed on Apr. 2, 2014, entitled: "Wireless Sensor Network", and provisional U.S. Patent Application 61/946,054, filed on Feb. 28, 2014, entitled: "Wireless Sensor Network", the entire contents of which are hereby incorporated by reference.

BACKGROUND

This description relates to operation of sensor networks such as those used for security, intrusion and alarm systems installed on commercial or residential premises.

It is common for businesses and homeowners to have a security system for detecting alarm conditions at their premises and signaling the conditions to a monitoring station or to authorized users of the security system. Security systems often include an intrusion detection panel that is electrically or wirelessly connected to a variety of sensors. Those sensors types typically include motion detectors, cameras, and proximity sensors (used to determine whether a door or window has been opened). Typically, such systems receive a very simple signal (electrically open or closed) from one or more of these sensors to indicate that a particular condition being monitored has changed or become unsecure.

Constrained computing devices as used herein are devices with substantially less persistent and volatile memory than other computing devices, sensors, etc. used in a detection system. Currently examples of constrained devices would be those with less than about a megabyte of flash/persistent memory, and less than about 10-20 kbytes of RAM/volatile memory).

Updating firmware on such devices typically involves boot-loading that requires transmission of the entire executable code image over a communications interface even if only a portion of the code changes.

SUMMARY

Constrained devices are characterized as such and are configured in this manner generally due to cost/physical configuration considerations. These types of devices generally have a static software image (i.e., the logic programmed into the device is always the same). Traditionally constrained devices are deployed with associated sensors and, additionally, may be deployed with communications interfaces (wired or wireless) to provide a distributed data collection network that reports collected data as "events" to a central hub (computer/control panel) or to a remote server via a hub and a network connection, e.g., an Internet connection.

It is difficult to update the firmware on such a constrained device, and when such updates occur it is through a "bootloader," which receives the new firmware via a communications link and stores the new firmware in persistent memory, validates the new code, and then performs a special rebooting process (controlled by the bootloader) to replace the old code or "image" with the new image. However, updating firmware using traditional boot-loading requires transmission of the entire executable code image over the communications interface even if only a portion of the code changes. However, this approach wastes valuable communications bandwidth.

Thus, this boot-loading process has drawbacks because even small changes in stored parameters or computer code require that the entire image be replaced. Bootloading is time-consuming and potentially dangerous to the overall system because if anything goes wrong (e.g., power loss) when writing the new code to the final location, the device can be rendered useless, requiring factory repair. Also bootloading necessarily means "rebooting" the device which requires the re-initialization of all of its peripheral drivers and communication links, network connections, reconfiguring of applications, and so forth. Because of these drawbacks bootloading and firmware updates relying on bootloading should not be part of day-to-day operation of constrained devices.

According to an aspect, a computer program product is tangibly stored on a computer readable hardware storage device. The computer program product is for managing constrained sensor devices on a network and includes instructions to cause a processor to manage a dynamic set of user-defined independent executable functions or tasks that are either built into a loaded image or downloaded during normal operation of a constrained sensor device, by schedule functions to execute on the constrained sensor device according to availability and priority of the functions relative to other functions.

Such dynamic programming techniques enable a constrained device to change its behavior and capabilities without the time-consuming and problematic process of bootloading. Depending on situations and needs over time, transient sub-programs are added and removed, effectively changing the executable code the device contains. For many applications this may need to be done with little notice and in a way which is not conducive to traditional bootloading. For example, the device may need to load new code many times in a day to support an application or, stated more properly, a set of related applications. During code update the device may need to be available for other work (e.g., interrupt-based collection, reporting of sensor events and communications with external devices). These considerations lead to the requirement that code updates be made in a way which is (1) safe; (2) rapid; (3) real-time; (4) without any interfering with normal operations (5) without rebooting of the device.

Dynamic programming of persistent memory is not possible with any traditional real-time operating system ("RTOS"), and certainly not with any RTOS thus far implemented for constrained devices. These traditional operating systems establish code locations and links (pointer values, return addresses, etc.) at the time of linking in preparation of the executable code image. This approach is intrinsically static in nature and not conducive to a system in which new executable code is introduced into the image, on the fly, without a reboot.

Disclosed is a new approach to an operating system for a constrained device by the use of that operating system to enable dynamic programming of constrained devices.

The details of one or more embodiments of the invention are set forth in the accompanying drawings and the description below. Other features, objects, and advantages of the invention is apparent from the description and drawings, and from the claims.

DETAILED DESCRIPTION

Described herein are examples of network features that may be used in various contexts including, but not limited to, security/intrusion and alarm systems. Example security systems may include an intrusion detection panel that is electrically or wirelessly connected to a variety of sensors. Those sensors types may include motion detectors, cameras, and proximity sensors (used, e.g., to determine whether a door or window has been opened). Typically, such systems receive a relatively simple signal (electrically open or closed) from one or more of these sensors to indicate that a particular condition being monitored has changed or become unsecure.

For example, typical intrusion systems can be set-up to monitor entry doors in a building. When a door is secured, a proximity sensor senses a magnetic contact and produces an electrically closed circuit. When the door is opened, the proximity sensor opens the circuit, and sends a signal to the panel indicating that an alarm condition has occurred (e.g., an opened entry door).

Data collection systems are becoming more common in some applications, such as home safety monitoring. Data collection systems employ wireless sensor networks and wireless devices, and may include remote server-based monitoring and report generation. As described in more detail below, wireless sensor networks generally use a combination of wired and wireless links between computing devices, with wireless links usually used for the lowest level connections (e.g., end-node device to hub/gateway). In an example network, the edge (wirelessly-connected) tier of the network is comprised of resource-constrained devices with specific functions. These devices may have a small-to-moderate amount of processing power and memory, and may be battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Figure 1:
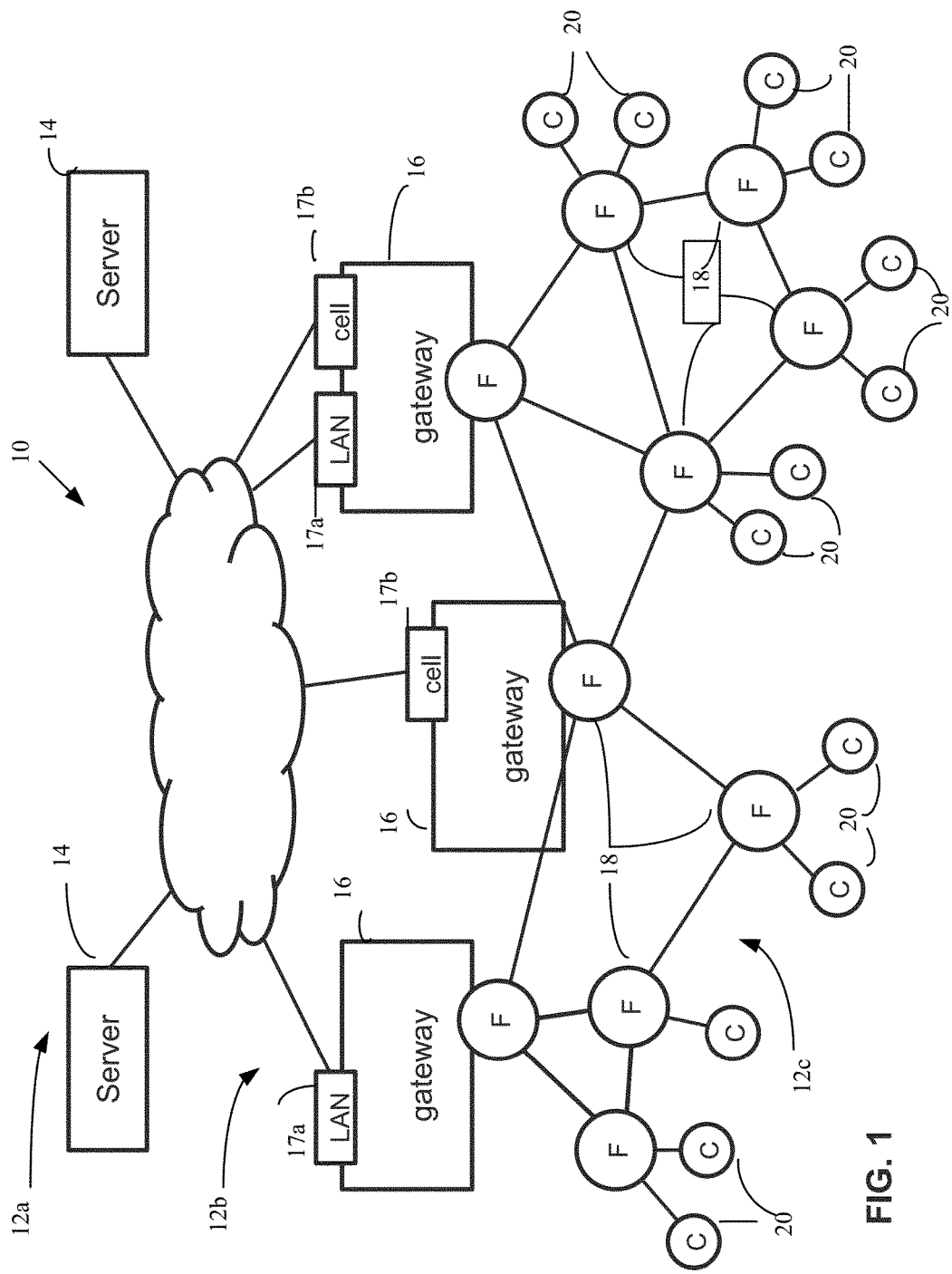
FIG. 1 is a schematic diagram of an exemplary networked security system.

Referring now to FIG. 1, an exemplary (global) distributed network topology for a Wireless Sensor Network (WSN) is shown. In FIG. 1 the distributed network 10 is logically divided into a set of tiers or hierarchical levels 12a-12c.

In an upper tier or hierarchical level 12a of the network are disposed servers and/or virtual servers 14 running a "cloud computing" paradigm that are networked together using well-established networking technology such as Internet protocols or which can be private networks that use none or part of the Internet. Applications that run on those servers 14 communicate using various protocols such as for Web Internet networks XML/SOAP, RESTful web service, and other application layer technologies such as HTTP and ATOM. The distributed network 10 has direct links between devices (nodes) as shown and discussed below.

The distributed network 10 includes a second logically divided tier or hierarchical level 12b, referred to here as a middle tier that involves gateways 16 located at central, convenient places inside individual buildings and structures. These gateways 16 communicate with servers 14 in the upper tier whether the servers are stand-alone dedicated servers and/or cloud based servers running cloud applications using web programming techniques. The middle tier gateways 16 are also shown with both local area network 17a (e.g., Ethernet or 802.11) and cellular network interfaces 17b.

The distributed network topology also includes a lower tier (edge layer) 12c set of devices that involve fully-functional sensor nodes 18 (e.g., sensor nodes that include wireless devices, e.g., transceivers or at least transmitters, which in FIG. 1 are marked in with an "F") as well as constrained wireless sensor nodes or sensor end-nodes 20 (marked in the FIG. 1 with "C"). In some embodiments wired sensors (not shown) can be included in aspects of the distributed network 10.

Figure 2:
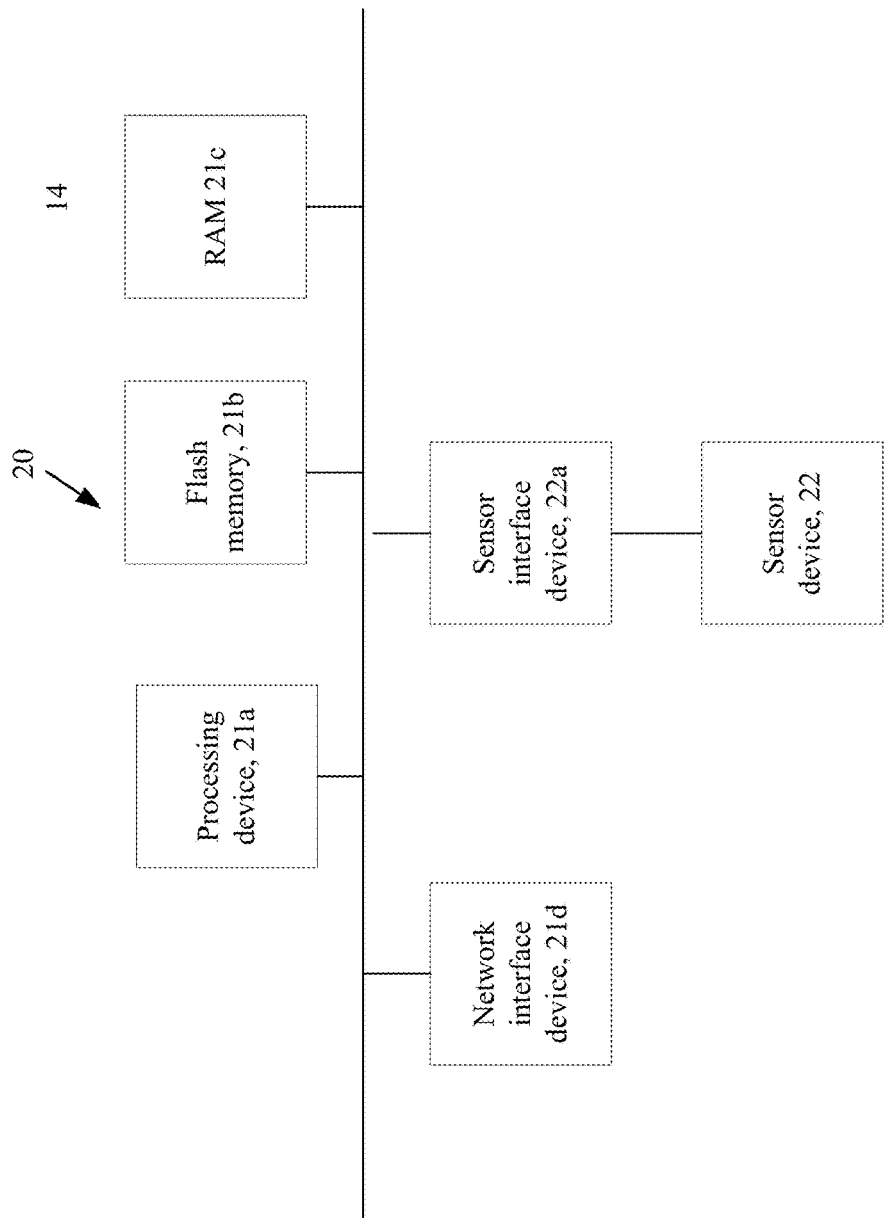
FIG. 2 is a block diagram of constrained device.

Referring momentarily to FIG. 2, a generic constrained computing device 20 is shown. A constrained device 20 as used herein is a device having substantially less persistent and volatile memory other computing devices, sensors, systems in a particular networked detection/sensor/alarm system. Constrained device 20 includes a processor device 21a, e.g., a CPU and or other type of controller device that executes under an operating system, generally with 8-bit or 16-bit logic rather than the 32- and 64-bit logic used by high-end computers and microprocessors. The constrained device 20 has a relatively small flash/persistent store 21b and volatile memory 21c in comparison with other the computing devices on the network. Generally the persistent store 21b is about a megabyte of storage or less and volatile memory 21c is about several kilobytes of RAM memory or less. The constrained device 20 has a network interface card 21d that interfaces the constrained device 20 to the network 10. Typically a wireless interface card is used, but in some instances a wired interface could be used. Alternatively, a transceiver chip driven by a wireless network protocol stack (e.g., 802.15.4/6LoWPAN) can be used as the (wireless) network interface. These components are coupled together via a bus structure. The constrained device 20 also includes a sensor 22 and a sensor interface 22a that interfaces to the processor 21a. Sensor 22 can be any type of sensor type device. Typical types of sensors include temperature, simple motion, 1- 2- or 3-axis acceleration force, humidity, pressure, selective chemical, sound/piezo-electric transduction, and/or numerous others, implemented singly or in combination to detect complex events.

The disclosed implementations of a constrained device 20 can follow the current constraints on flash/persistent storage memory and RAM memory and less than 10-20 kilobytes of RAM/volatile memory, but can have more depending on configuration and in some instances the operating system. These constrained devices 20 are configured in this manner; generally due to cost/physical configuration considerations. These types of constrained devices 20 generally have a static software image (i.e., the logic programmed into the constrained device is always the same).

Referring back to FIG. 1, in a typical network, the edge (wirelessly-connected) tier of the network is largely comprised of highly resource-constrained devices with specific functions. These devices have a small-to-moderate amount of processing power and memory, and often are battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Each gateway is equipped with an access point (fully functional node or "F" node) that is physically attached to that access point and that provides a wireless connection point to other nodes in the wireless network. The links (illustrated by lines not numbered) shown in FIG. 1 represent direct (single-hop MAC layer) connections between devices. A formal networking layer (that functions in each of the three tiers shown in FIG. 1) uses a series of these direct links together with routing devices to send messages (fragmented or non-fragmented) from one device to another over the network.

The WSN 10 implements a state machine approach to an application layer that runs on the lower tier devices 18 and 20. Discussed below is an example of a particular implementation of such an approach. States in the state machine are comprised of sets of functions that execute in coordination, and these functions can be individually deleted or substituted or added to in order to alter the states in the state machine of a particular lower tier device.

The WSN state function based application layer uses an edge device operating system (not shown, but such as disclosed in the above mentioned provisional application) that allows for loading and execution of individual functions (after the booting of the device) without rebooting the device (so-called "dynamic programming"). In other implementations, edge devices could use other operating systems provided such systems allow for loading and execution of individual functions (after the booting of the device) preferably without rebooting of the edge devices.

RTOS for Constrained Devices

Figure 3:
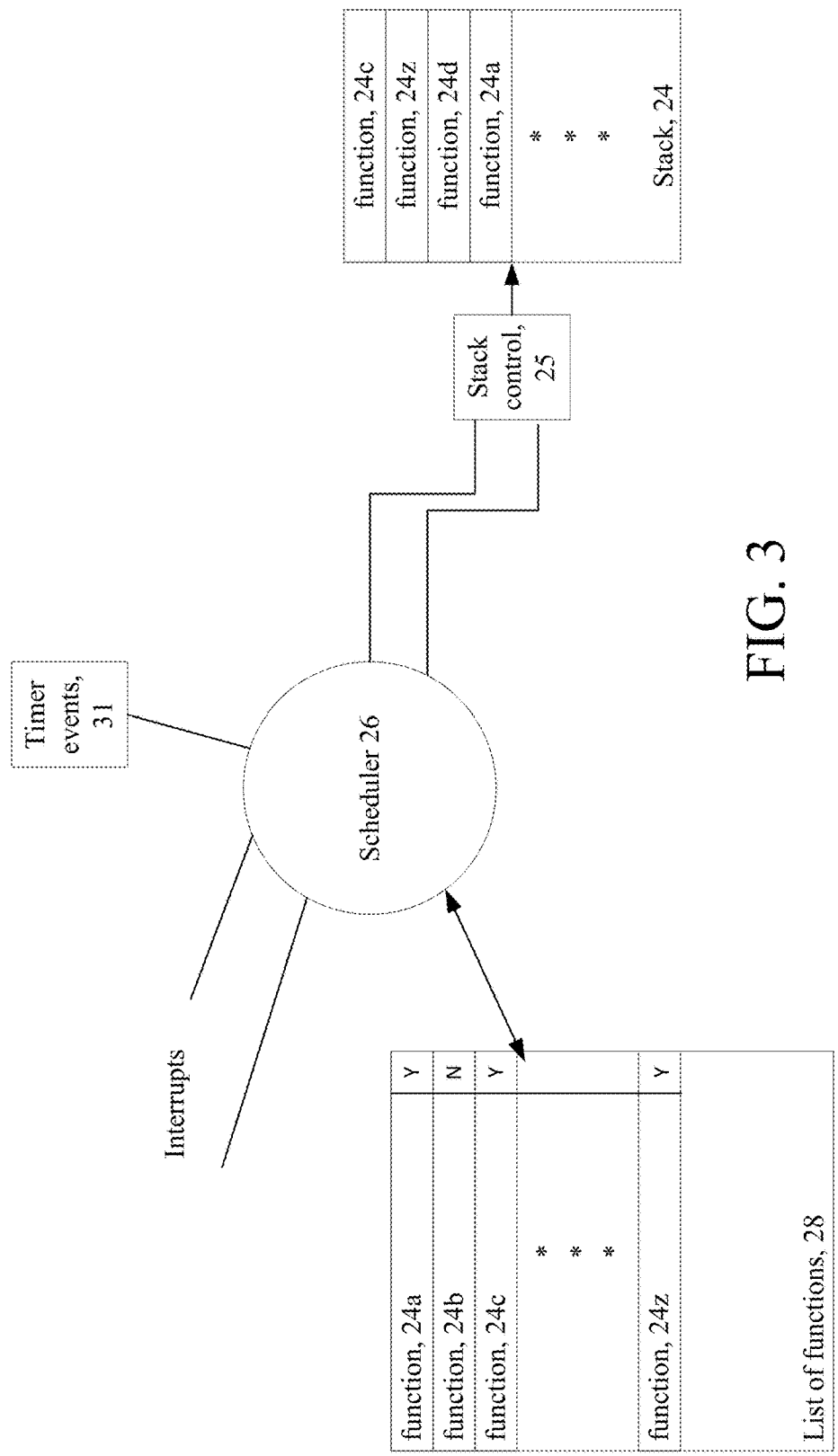
FIG. 3 is a block diagram useful in understanding a stack structure.

Referring to FIG. 3, stack process details for an operating system for constrained device 20 that includes wireless dynamic programming and support are shown. The constrained device 20 includes a real-time operating system ("RTOS") for executing and otherwise managing a dynamic set of user-defined independent executable functions or tasks that are either built into a loaded image (software and RTOS that executes on the constrained device) or that are downloaded during normal operation of the constrained device 20 or a combination of the two, with the former (built into the image) using as subroutines instances of the latter (downloaded during operation).

Stack Management

The RTOS is for constrained devices and uses a scheduling function 26 referenced through a management structure (e.g., an array or linked list of pointers to function locations), according to availability (readiness of the function to run) and priority (the criticality of the function relative to other functions). This scheduler 26 function periodically evaluates functions that are not currently running on the constrained device, e.g., as in a list, 28 to determine whether any of these functions are ready to run. In addition the scheduler 26 is responsive to interrupt(s) that indicated a function or functions are ready to run by either supplying data to a pended function or counting down of a timer event 31 for a function that has suspended execution.

In either case, if a function is found ready to run that is of higher priority than the function currently running (or of equal priority if the current function has pended execution waiting for data) has identified, that identified function is run without the prior saving of the old function to another place in RAM (i.e., without traditional context switching or saving of the processor's operating register values). A stack 24 has functions stored, e.g., in order 24c, 24z, 24d and 24a, according to respective priorities. When a new function is ready to run of the highest priority, e.g., 24c, the stack functions of remaining functions, e.g., 24z, 24d and 24a simply remain in place on the single stack 24 of the processor as the newly running, preempting function pushes its data on top of the active function's stack.

When the new function completes running and returns, all its stack usage is popped via stack control 25 and the old function, e.g., 24z, resumes running, oblivious to the interruption, as transparently as if a traditional context switch had occurred. Thus, the scheduler 26 uses a single processor stack rather than formal context switching to save the state of pre-empted functions.

This saves a non-trivial amount of RAM by not having multiple stacks, thus allowing for more independently executable functions, as well as saving the processor time required to do the formal context switching and it simplifies the logic and, therefore, the code size associated with the scheduler 26.

Dynamic Programming

The disclosed operating system is conducive to dynamic programming because new functions (executable functions loaded into the device via a communications link) can be added to the scheduler's list of executable functions by simply adding the new functions to the management structure (array or linked list of function pointers), updating the related readiness and priority information in the scheduler variables, and producing any necessary links between old and new code (return addresses, global variable locations, etc.). If and when a dynamic function is no longer needed, the dynamic function can simply be removed from the management structure and it links dissolved and memory reclaimed.

The use of dynamic programming methods running on top of the operating system described below allows for a constrained device to effectively use of a set of executable functions many times larger than would fit into its memory at any single instant in time. The operating system below includes methods by which a node requesting executable code that the node needs and does not possess to obtain the code, while also guaranteeing that the node's current set of executable functions are all of the proper type and version (executable set self-consistency). Furthermore, executable code can be cached in network locations convenient for rapid transfer to constrained devices as soon as the executable code is needed by the constrained devices. Also described below are methods for managing the "freshness date" and expiration of executable code for that code which should be used for only a limited period of time in the constrained device.

Figure 4:
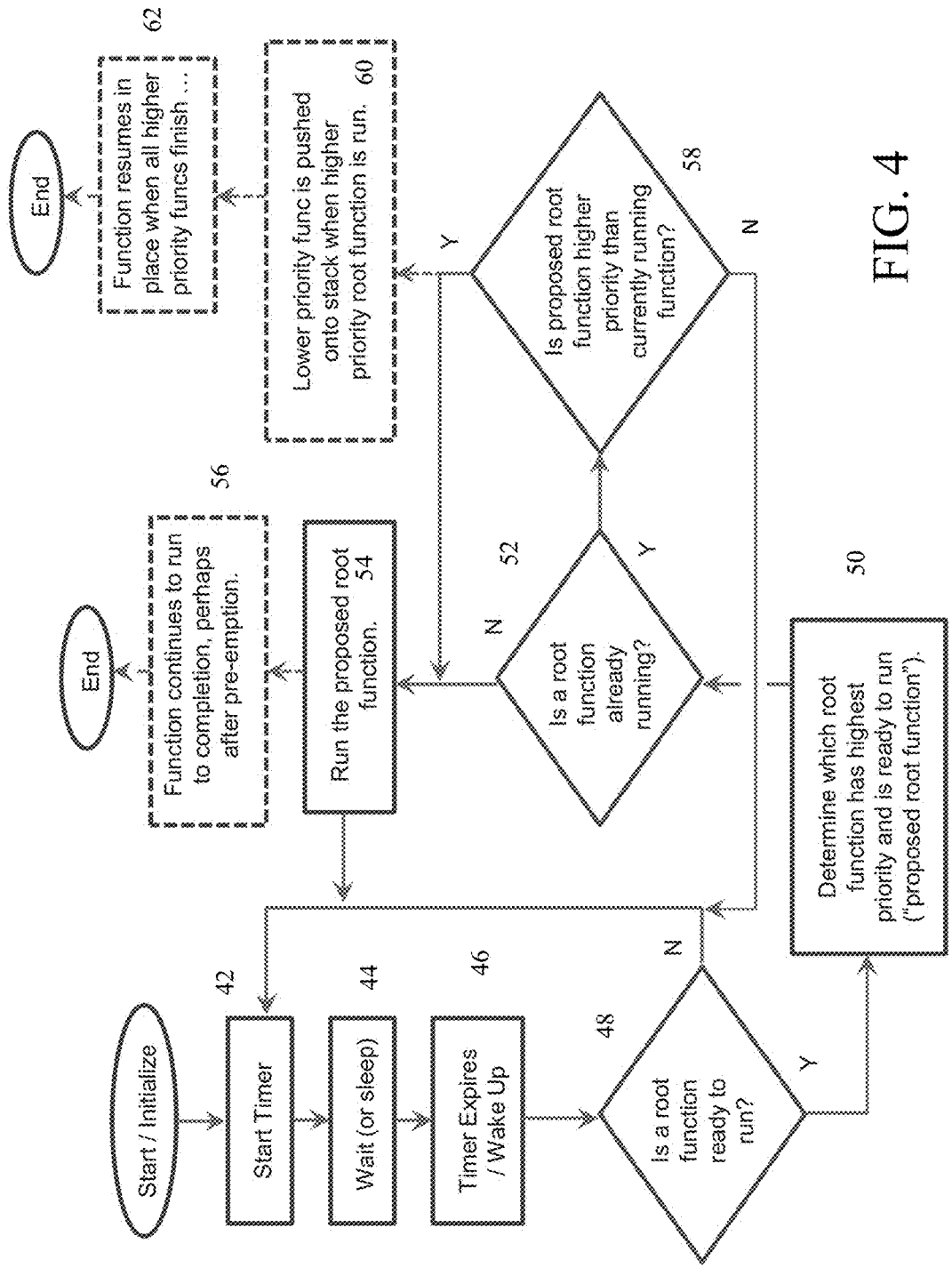
FIG. 4 is a flow chart of scheduler processing in a real time operating system.

Referring now to FIG. 4 actions taken by the scheduler 26 of the operating system to manage the prioritized execution of a set of root functions is shown. The functions managed directly by the scheduler 26 are referred to as "root functions" because they themselves can call other functions, which in turn may call various other functions, and this branching of function calls has a structure analogous to the branching of limbs in a tree.

Ultimately all function execution stems back, like the branches of a tree, to the primary/first/root function that was called (i.e., executed) initially by the scheduler 26. The distinction between a root function and a regular (non-root) function is that a non-root function is not managed by the scheduler 26, and can only run when explicitly called by the currently running function. A root function is somewhat like standard operating systems' threads or tasks.

The scheduler 26 may alternatively simply round-robin through the root functions from the highest in priority to the lowest, executing each that is ready to run; or the scheduler 26 may be configured (as is presumed to be the most likely scenario) to execute the highest in priority ready to run and after executing that, again seek the highest in priority ready to run, and keep repeating that sequence until reaching and executing the root function lowest in priority.

In some embodiments, the lowest priority root function will, for power-constrained devices, start a timer and wait (enter sleep mode) and when the device is awakened by some configured interrupt, the scheduling sequence is again performed; in non-power-constrained devices, the lowest priority function would simply service a watchdog timer, or perform self-test, or both, and then the scheduling sequence would repeat.

Thus, as shown in the FIG. 4, a timer is set up 42 and run with the purpose of controlling the frequency with which the scheduler 26 examines the state of the set of root functions. The scheduler 26 waits (enter sleep mode) 44 for a scheduler timer event. When the timer expires 46 the scheduler 26 determines 48 whether or not ANY of the root functions in its list is ready to run (e.g., via a variable associated with each root function with possible values of "ready to run", "pended", "killed", etc.). If any root function is ready to run, the scheduler 26 needs next to determine, which of all of the ready-to-run root functions, is the function with the highest priority 50 (which becomes the "proposed root function"). If no other root function is running, 52 the proposed root function is run immediately, runs to completion, and exits 54 (although it may during the course of running be interrupted by being pre-empted by an even higher priority root function using the process described here 56).

Figure 7:
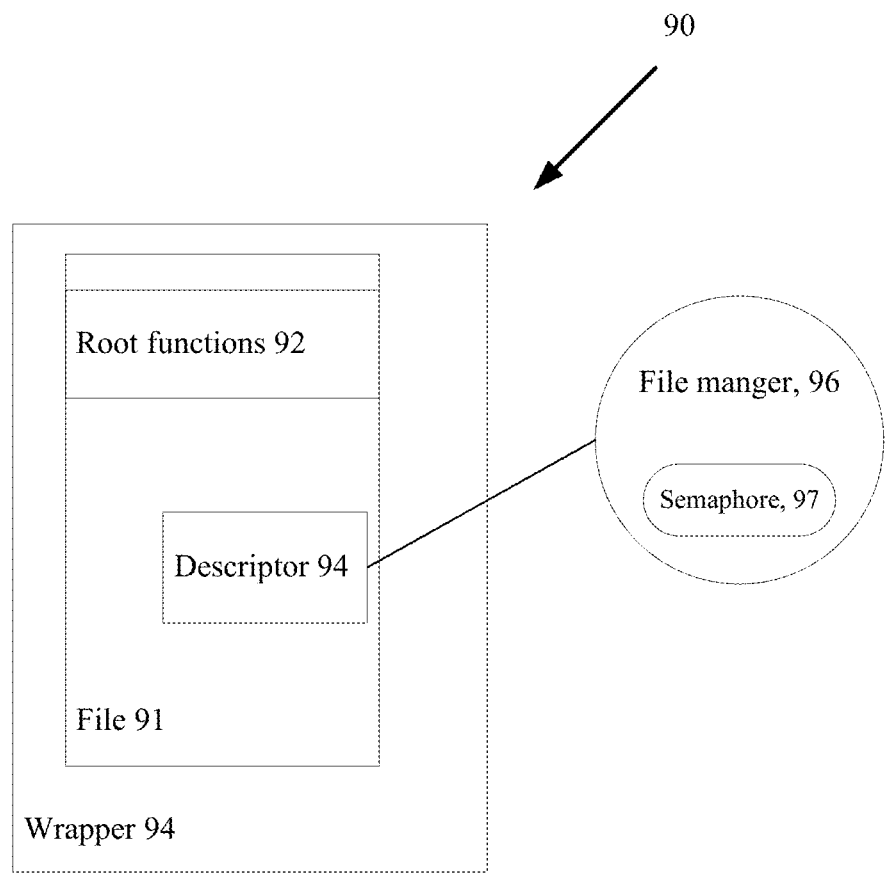
FIG. 7 is block diagram showing function encapsulation.

If a root function is already running then the scheduler 26 compares 58 priorities of the currently running root function and the proposed root function. If the proposed root function's priority is lower, nothing happens and the scheduler 26 goes back to sleep to await another scheduler timer wakeup event. If on the other hand the proposed root function's priority is higher, the scheduler 26 immediately runs 60 the proposed root function. The dotted line boxes and arrows in the FIG. 7 show processor behavior in response to the running of a new root function (e.g., the currently running root function is pushed onto the stack). The function that was running resumes 62 in place when all higher priority functions have finished processing.

Figure 5:
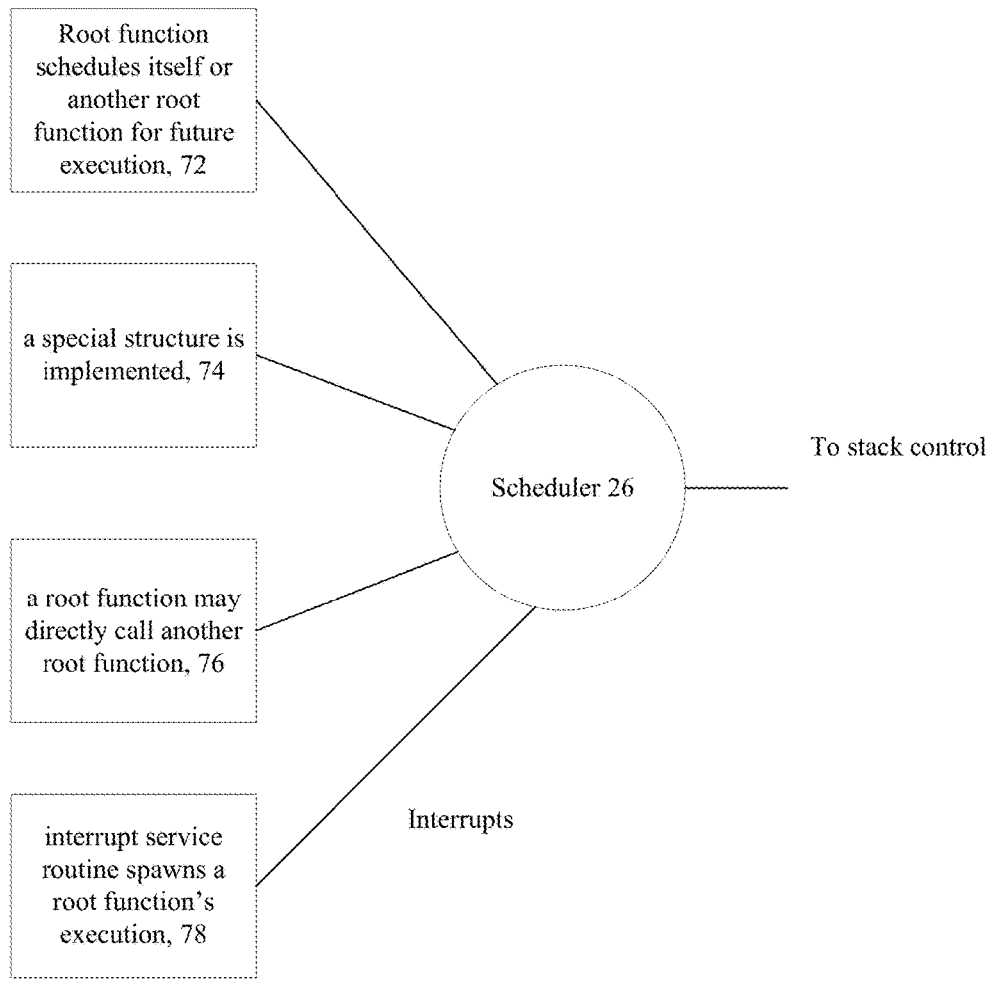
FIG. 5 is block diagram useful in understanding scheduling.

Referring now to FIG. 5, other mechanisms, e.g., here four mechanisms shown can spawn a root function. For example, a root function can schedule itself or another root function's execution in the future which will be spawned from a periodic timer's interrupt, a special structure that is implemented; a ring buffer coupled with a pointer to a root function that is the sole consumer of its data, will awaken that consuming root function, should it be in a pended state, upon being provided with a threshold amount of data, a root function may directly call another root function for, for example, the arrival of data that other root function should process, or an interrupt service routine may spawn a root function's execution. In all these instances, the scheduler 26 immediately executes the root function requested to spawn if that root function has of an equal or greater priority than the root function then running Otherwise, if the former has a lower priority than the latter, the former is put into a state "ready to run" that permits it to run the next chance it has to be scheduled.

Figure 6:
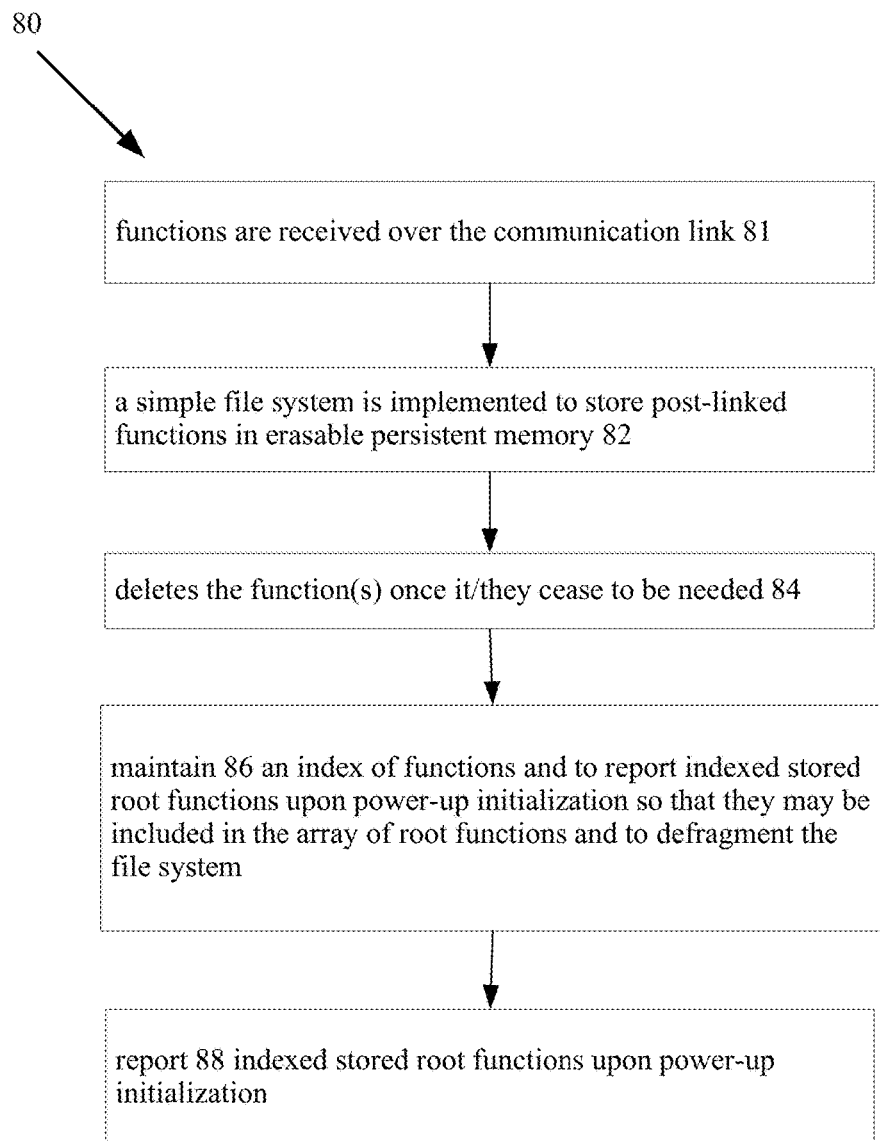
FIG. 6 is flow chart showing processing for functions.

Referring to FIG. 6, for implementation 80 of post-linked functions (i.e., functions loaded over a communications link) especially for post-linked root functions several mechanisms are provided. For example, when the functions are received over the communication link 81, a simple file system is implemented to store post-linked functions in erasable persistent memory (e.g., flash) 82 when the functions are received over the communication link, schedule deletes the function(s) once it/they cease to be needed and maintain 86 an index of functions and to report 88 indexed stored root functions upon power-up initialization so that the functions may be included in the array of root functions and defragment the file system.

Defragmenting the file system requires locks (binary semaphores) to prevent either an executing function from being relocated consequent to defragmentation or for a function that is being moved during defragmentation from being executed.

Post-linked functions require additional data, as explained below, in order to be utilized and, thus, they need to be wrapped with other data in a file; non-root post-linked functions require some but fewer data, as implied below, in such a wrapper.

Post-linked root functions need to be added to the array of root functions when they are received into to the file system and they need to be deleted from that array when ceasing to be used, thus requiring that that array be a linked list. Thus, post-linked root functions are scheduled exactly like root functions linked into the application with the scheduler 26.

Referring now to FIG. 7, post-linked root functions, in order to be in the array of root functions, require a descriptor structure as other root functions. However, because the descriptor structure needs to include addresses such as those of the executable code for the root function, the descriptor would necessarily not exist verbatim in the file in which the post-linked root function resides because its location in memory is not known until the file manager writes the location.

This problem is addressed by including a wrapper 94 of the file 91 containing the function 92, a structure 96 from which the post-linked function's descriptor can be constructed in RAM. While other root functions' descriptors reside in ROM and need never to be altered, a post-linked root function's descriptor needs to be altered whenever the function is relocated for defragmentation and, so, when a file manager 96 seeks to relocate the function, it acquires the appropriate semaphore 97 and adjusts the descriptor in addition to moving the file containing the function.

Post-linked functions that are not root functions likewise have a relocatable base address and in the process of relocation need to locked against execution and while executing need to be locked against relocation, but since there is no root function descriptor constructed for it, its relocation involves a subset of a root function's relocation.

The operating system additionally needs to allocate some RAM for post-linked functions, all requiring storage of their base address of their ROM and RAM, explained and described below, and, optionally, any global variables that statically persist for the life of the function, and for root functions, the descriptor described above. Real-time systems do not typically have dynamically allocated memory because this introduces non-deterministic behavior into the system.

The scheduler 26, furthermore, is constrained by not having the resources for garbage collection (memory recovery) which is expensive in terms of both code footprint and execution time.

Figure 8:
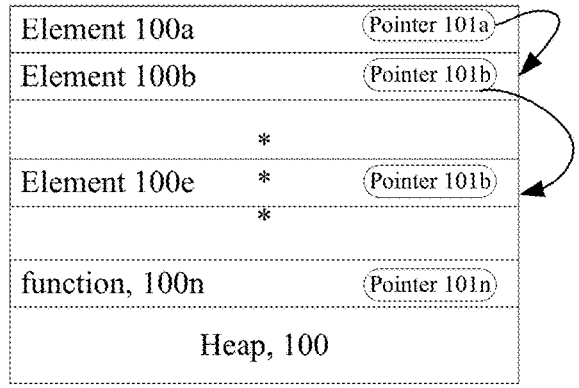
FIG. 8 is block diagram of a heap.

Referring now to FIG. 8, the operating system implements a specialized heap 100, therefore, for post-linked functions to obtain their root function variable data and any other variable data needed. An allocation from the heap 100 can be made only during the initialization of a post-linked function and then only once for each initialization function call. Assuming the device has a single, contiguous bank of RAM, the heap grows from the opposite end of RAM as does the stack 24, growing toward the stack 24, and shrinks back when the most recently added post-linked function terminates. Because the heap 100 exists only to provide RAM to post-linked functions, its structure can be, and is, inexorably intertwined with its reason for existence.

Starting from the first available position in RAM, each element 100a-100n contains a pointer to the start of the next valid element since its size cannot necessarily be determined from the previous field because the latter may reflect a hole consequent to a post-linked function's removal.

Figure 8A:
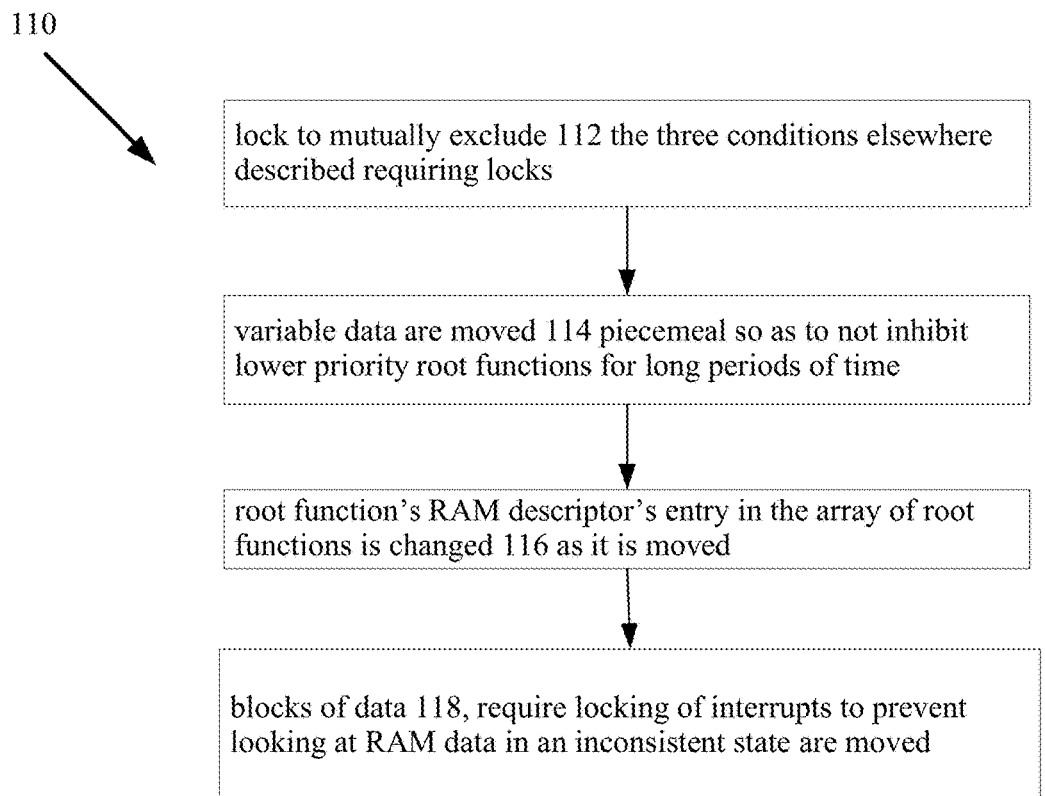
FIGS. 8A-8C are flow charts of processing involving the heap.

Referring now to FIG. 8A, such holes are cleaned up using a high-priority root function 110 built into the scheduler 26. This root function uses a fourth lock to mutually exclude 112 the three conditions elsewhere described requiring locks. Once the lock is obtained, the variable data are moved 114 piecemeal so as to not inhibit lower priority root functions for long periods of time. A root function's RAM descriptor's entry in the array of root functions needs to be changed 116 as it is moved and that, together with certain other blocks of data 118, require locking of interrupts to prevent looking at RAM data in an inconsistent state, which would wreak havoc in the scheduler 26. The blocks of data are the base addresses of the function's RAM and ROM to restore, as described below, when the function is executed, the RAM copy of the root function's descriptor, the variable data pointed to by the root function's descriptor, and to local data for the root function.

Figure 8B:
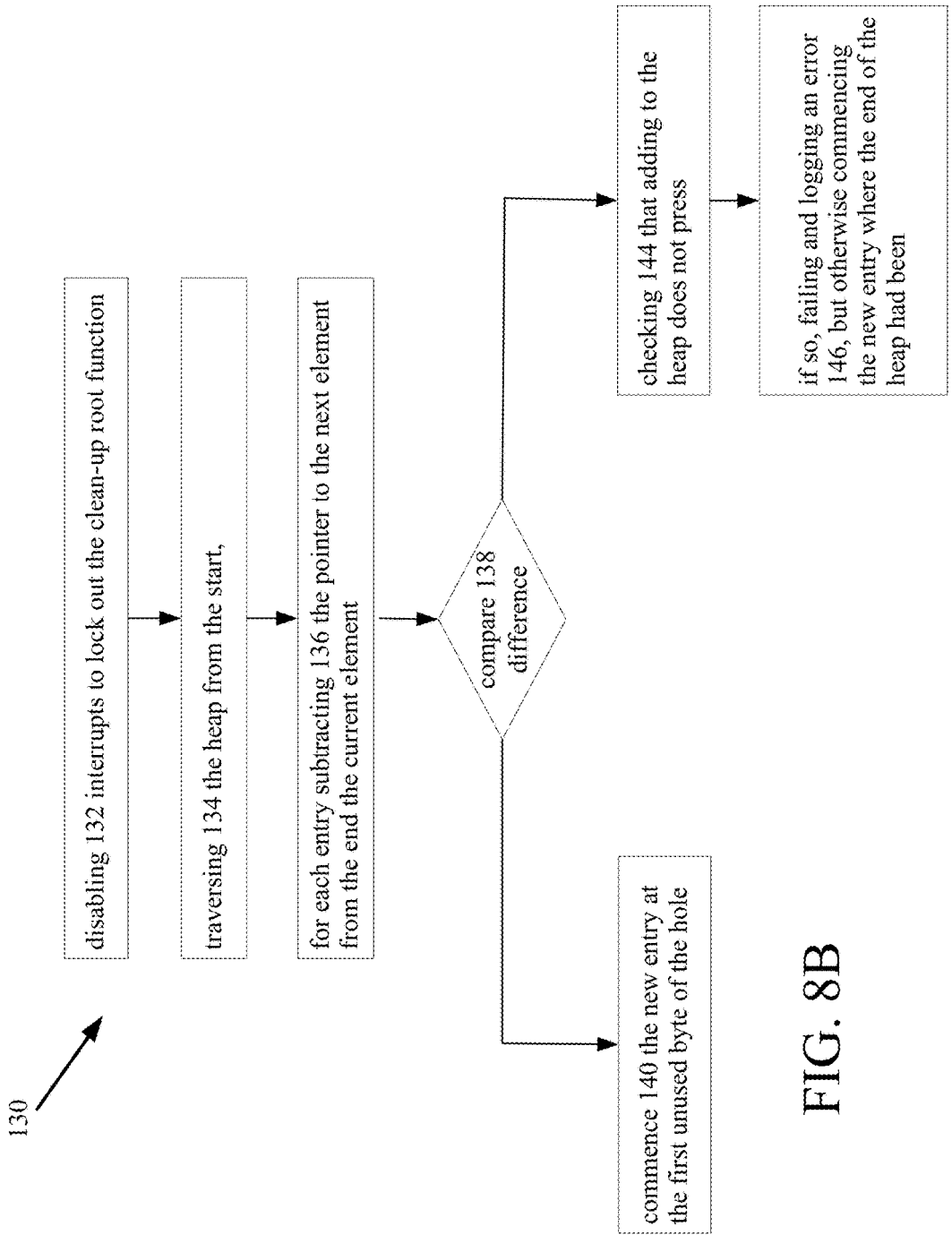

Referring now to FIG. 8B, adding 130 an element to the heap entails disabling 132 interrupts to lock out the clean-up root function described above, traversing 134 the heap from the start, and for each entry subtracting 136 the pointer to the next element from the end the current element and comparing 138 the difference to the requested number of bytes and if the latter is smaller than the former, then commencing 140 the new entry at the first unused byte of the hole but otherwise, if the last entry of the heap is encountered, 142 checking 144 that adding to the heap does not press closely against the stack (the tolerance of how close being configured by the application) and, if so, failing and logging an error 146, but otherwise commencing the new entry where the end of the heap had been.

For a post-linked root function, the descriptor needs to now be constructed and other RAM initialized, the details of which are not described here for the sake of brevity.

Figure 8C:
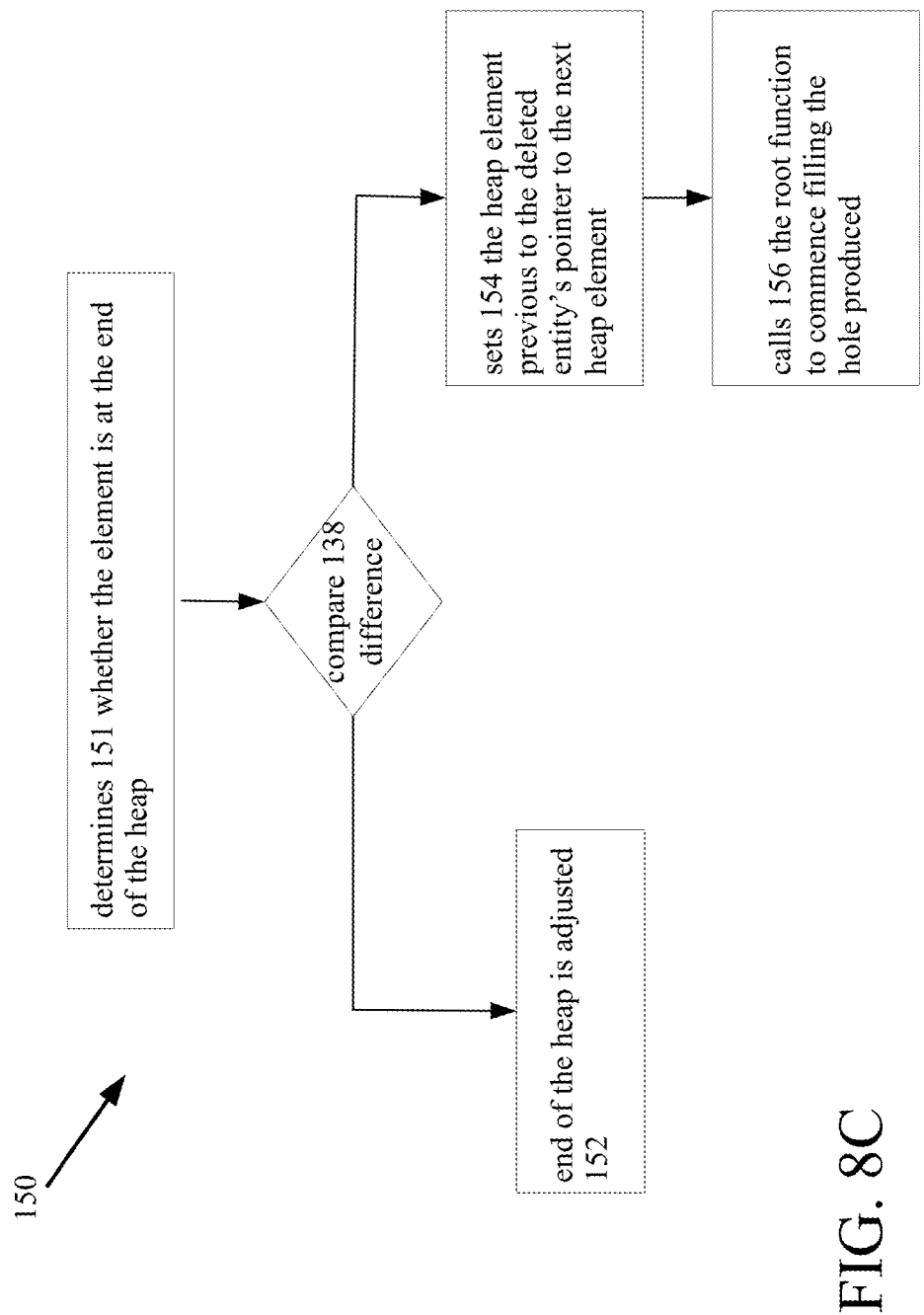

Referring now to FIG. 8C, to remove 150 an element from the heap, the scheduler 26 determines 151 whether the element is at the end of the heap, in which case the end of the heap can simply be adjusted 152, but otherwise, sets 154 the heap element previous to the deleted entity's pointer to the next heap element, i.e., unlinks the parameter's element out of existence thus producing a hole in the heap, and the calls 156 the root function referenced above to commence filling the hole produced. Thus, this is simpler than garbage clean-up algorithms but also being more constrained by the real-time requirements, has some innovative complexities.

Another lock, of short duration, is implemented for post-linked root functions so that when the scheduler 26 traverses the list of root functions, it will bypass any function that is in the process of having its descriptor or associated data moved.

The operating system also allows post-linked root functions to access utilities linked into the scheduler 26; especially, post-linked functions that communicate with other root functions and with device drivers. Since a post-linked function may not necessarily know where such functions are in any particular build, the scheduler 26 therefore implements a vector table for referencing any and all internal functions that a post-linked function can use.

Among the functions in the vector table are interfaces to ring buffers, optionally bound to a root function so that that root function can be awakened from a pended state and also so that post-linked root functions can publish such queues and other root functions or interrupt service routines can identify such queues that a post-linked function can instantiate from its allocated pseudo-global data. The publishing mechanism involves a linked list that commences with a pointer linked into the scheduler 26 that can point to an entry reserved for this purpose in the post-linked function's RAM data, and the latter can point into another such entity, and so forth. Any root function or interrupt service routine linked into the scheduler 26 needs to be programmed to expect such a link, and any pair of post-linked root functions expecting to communicate with each other need likewise to be programmed. A handshake mechanism is provided for by the functions that access the described queues.

The operating system provides for post-linked functions to use the internal global data by 1) requiring the function to declare all such data in a structure 2) produce a pointer to such a structure 3) not initialize that pointer. Each time the post-linked function is executed, the pointer to the said structure is supplied by the scheduler 26.

Thus, when a RAM clean-up is performed, the value of that pointer will differ from its value the previous time the post-linked function had been executed, but since its contents have been moved, that will be transparent to the post-linked function. Note that the pointer itself is anchored by the array of root functions or, for post-linked functions that are not root functions, anchored by a special descriptor ascertainable by traversing the entries in the heap.

The operating system likewise provides, for executing on a processor that does not support relocatable code, for post-linked functions to reference parts of themselves, e.g., branch functions or constants, by a similar mechanism whereby pointer to those parts are gathered into a structure, etc., as for global data, but let it be noted that the author of such a function on such a device needs to, therefore, call all branch functions via pointers to them.

The scheduler 26 can inhibit the execution of post-linked root functions that are locked, as described above, but for other post-linked functions that are being relocated in ROM or whose RAM is being moved, the scheduler 26 only notes this and returns an error code unique to the situation and, therefore, that it behooves an implementation of such a function to not use that unique code; this furthermore requires that the same type be returned by all non-root post-linked functions.

The utility of post-linked (dynamically loaded and executed) functions rests in the fact that it is not always possible to anticipate what logic is needed in a constrained device at the time the device is programmed and deployed. For example, the device may be a wireless sensor network node designed to sense, filter, and report very specific types of motion of a door, window, or moving asset (e.g., a hand truck or dolly). Because the specific motion filter algorithms/logic are different for each of these objects, and because it is difficult to pre-assign specific devices to specific uses without running into problems of high inventory costs and device staging in the supply chain, it would be inconvenient or expensive for the manufacturer of the device to be required to produce firmware-based motion filters specific to each of these very unique motion types.

Another approach is to produce basic firmware general enough to handle ALL motion event reporting, and factory-program the devices with this generic software. Then, after each node is deployed in the field (e.g., on a window, or a dolly), the required specific types of motion filters are sent to each node according to each node's unique deployment case. The context specific root functions (e.g., motion-type specific motion filters) are combined with other more generic root functions to comprise the software stack running on the device in the field.

Another situation which will certainly arise from time to time is that motion filters require "tuning" or changes in their firmware logic based on results observed in the field. Some filter behavior may be altered simply by changing threshold and other configuration parameter values, and this certainly does not require dynamic programming (loading of new executable code embodying new filtering logic), but there will be other times when the functional forms (math equations) used to implement the motion filtering algorithm need to change, and this can only be accomplished by either (1) including a large set of equation options during factory programming (which leads to an excessively large and likely infeasible code size), or (2) dynamically programming nodes in the field using the methods described. The latter approach is more useful since it can easily be done using iterative means, or even methods derived from machine learning and artificial intelligence concepts.

The nodes may be implemented using any appropriate type of computing device, such as a mainframe work station, a personal computer, a server, a portable computing device, or any other type of intelligent device capable of executing instructions, connecting to a network, and forwarding data packets through the network. The nodes can execute any appropriate computer programs to generate, receive, and transmit data packets for use on the network.

Figure 9:
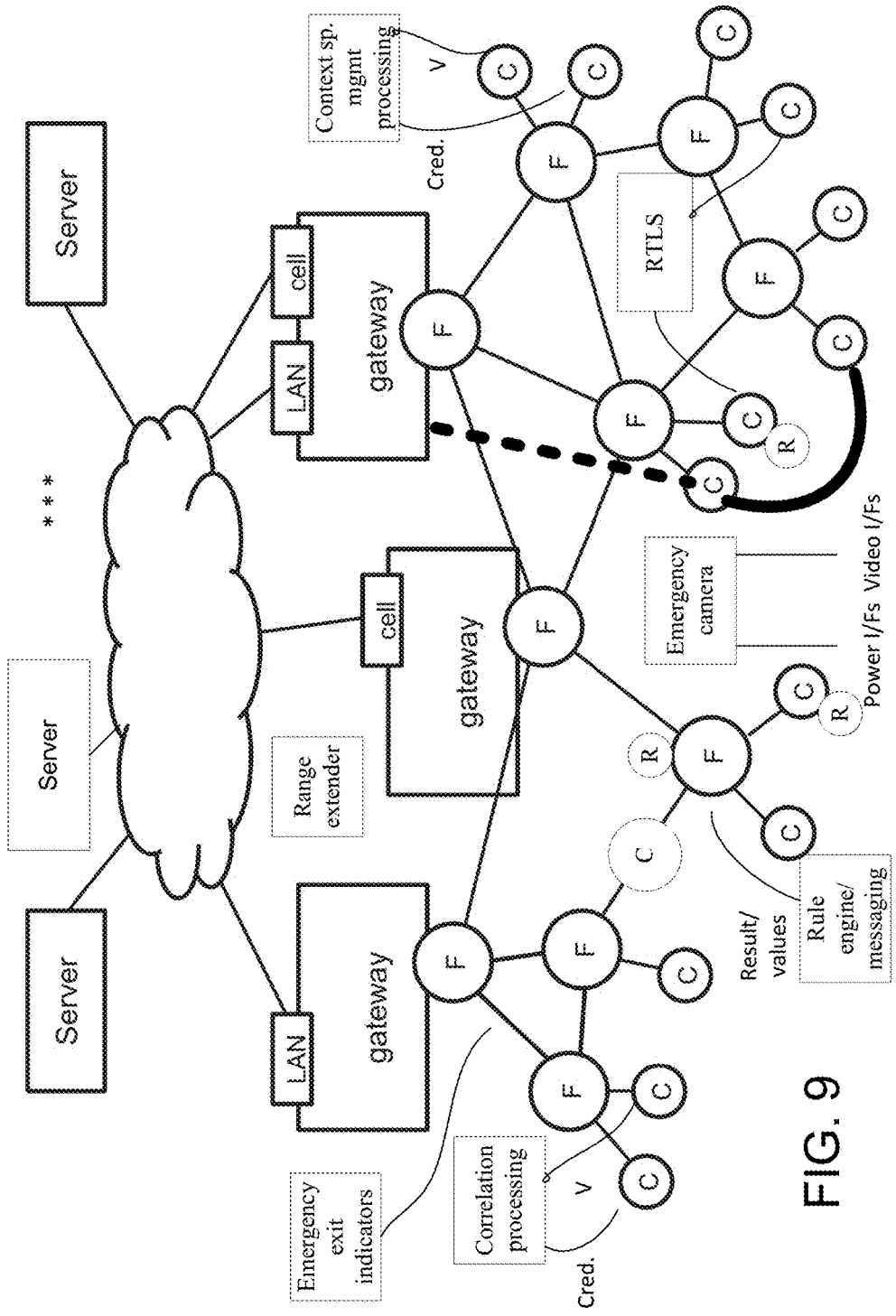
FIG. 9 is a block diagram of components of an example networked security system.

FIG. 9 shows an example of a security system having features of the WSN described with respect to FIG. 1 and having the various functionalities described herein. As shown in FIG. 9, correlation processing receives inputs from certain constrained nodes (although these can also be fully functional nodes). These inputs may include credential information and video information, and the correlation processing may produce correlated results that are sent over the network. Context management processing receives inputs from certain constrained nodes (although these can also be fully functional nodes) e.g., credential information and video and grouping information, and performs context processing with results sent over the network. The network supports operation of emergency exit indicators; emergency cameras as well as distributed rule processing and rule engine/messaging processing. Range extenders are used with e.g., gateways, and a real time location system receives inputs from various sensors (e.g., constrained type) as shown. Servers interface to the WSN via a cloud computing configuration and parts of some networks can be run as sub-nets.

The sensors provide in addition to an indication that something is detected in an area within the range of the sensors, detailed additional information that can be used to evaluate what that indication may be without the intrusion detection panel being required to perform extensive analysis of inputs to the particular sensor.

For example, a motion detector could be configured to analyze the heat signature of a warm body moving in a room to determine if the body is that of a human or a pet. Results of that analysis would be a message or data that conveys information about the body detected. Various sensors thus are used to sense sound, motion, vibration, pressure, heat, images, and so forth, in an appropriate combination to detect a true or verified alarm condition at the intrusion detection panel.

Recognition software can be used to discriminate between objects that are a human and objects that are an animal; further facial recognition software can be built into video cameras and used to verify that the perimeter intrusion was the result of a recognized, authorized individual. Such video cameras would comprise a processor and memory and the recognition software to process inputs (captured images) by the camera and produce the metadata to convey information regarding recognition or lack of recognition of an individual captured by the video camera. The processing could also alternatively or in addition include information regarding characteristic of the individual in the area captured/monitored by the video camera. Thus, depending on the circumstances, the information would be either metadata received from enhanced motion detectors and video cameras that performed enhanced analysis on inputs to the sensor that gives characteristics of the perimeter intrusion or a metadata resulting from very complex processing that seeks to establish recognition of the object.

Sensor devices can integrate multiple sensors to generate more complex outputs so that the intrusion detection panel can utilize its processing capabilities to execute algorithms that analyze the environment by building virtual images or signatures of the environment to make an intelligent decision about the validity of a breach.

Memory stores program instructions and data used by the processor of the intrusion detection panel. The memory may be a suitable combination of random access memory and read-only memory, and may host suitable program instructions (e.g. firmware or operating software), and configuration and operating data and may be organized as a file system or otherwise. The stored program instruction may include one or more authentication processes for authenticating one or more users. The program instructions stored in the memory of the panel may further store software components allowing network communications and establishment of connections to the data network. The software components may, for example, include an internet protocol (IP) stack, as well as driver components for the various interfaces, including the interfaces and the keypad. Other software components suitable for establishing a connection and communicating across network will be apparent to those of ordinary skill.

Program instructions stored in the memory, along with configuration data may control overall operation of the panel.

The monitoring server includes one or more processing devices (e.g., microprocessors), a network interface and a memory (all not illustrated). The monitoring server may physically take the form of a rack mounted card and may be in communication with one or more operator terminals (not shown). An example monitoring server is a SURGARD™ SG-System III Virtual, or similar system.

The processor of each monitoring server acts as a controller for each monitoring server, and is in communication with, and controls overall operation, of each server. The processor may include, or be in communication with, the memory that stores processor executable instructions controlling the overall operation of the monitoring server. Suitable software enable each monitoring server to receive alarms and cause appropriate actions to occur. Software may include a suitable Internet protocol (IP) stack and applications/clients.

Each monitoring server of the central monitoring station may be associated with an IP address and port(s) by which it communicates with the control panels and/or the user devices to handle alarm events, etc. The monitoring server address may be static, and thus always identify a particular one of monitoring server to the intrusion detection panels. Alternatively, dynamic addresses could be used, and associated with static domain names, resolved through a domain name service.

The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other implementations not specifically described herein are also within the scope of the following claims.

What is claimed is:
1. A computer program product tangibly stored on a computer readable non-transitory hardware storage device, the computer program product for managing constrained sensor devices on a network, the computer program product comprising instructions to cause a processor to:
   manage a dynamic set of user-defined independently executable functions or tasks that are either built into a loaded image or downloaded during normal operation of a constrained sensor device, to further cause the processor to:
      add a new function to a management structure that comprises an array or a linked list of function pointers;
      update readiness and priority information in scheduler variables; and produce links between old and new code; and
   schedule functions that are referenced through the management structure, to execute on the processor in the constrained sensor device, according to availability based on readiness information and priority of the scheduled functions relative to other functions obtained from the management structure, without saving context that includes register values of registers in the processor of a prior function executing on the processor in the constrained sensor device stored on a stack in random access memory to a different location in the random access memory, with the context including processor operating register values of the prior function, when a next function is identified as ready to run and the next function has a higher priority than the prior function executing on the constrained sensor device.

2. The computer program product of claim 1 wherein the computer program product is a real-time operating system for execution on the constrained sensor device.

3. The computer program product of claim 1 wherein the schedule instructions periodically evaluate the functions not currently running to determine whether any of these are ready to run.

4. The computer program product of claim 1 wherein an interrupt is used to determine that a function is ready to run by either a supplying of data to a pended function or a counting down of a timer event for a function that has suspended itself.

5. The computer program product of claim 1, further comprising to cause the processor to generate:
the stack, with functions stored according to respective priorities, and when the next function is found ready to run and is of higher priority than the prior function, the next function pushes its data on top of the stack.

6. The computer program product of claim 5 wherein when the next function completes running and returns, all its stack usage is popped and the prior function resumes running.

7. A method comprises:
managing by a processor including registers, and which controls a constrained sensor device a dynamic set of user-defined independent executable functions or tasks that are either built into a loaded image or downloaded during normal operation of the constrained sensor device, by:
adding a new function to a management structure that comprises an array or a linked list of function pointers;
updating readiness and priority information in scheduler variables; and
producing links between old and new code; and
scheduling functions that are referenced through the management structure, to execute on the processor in the constrained sensor device according to availability based on readiness information and priority of the scheduled functions relative to other functions, which are obtained from the management structure without saving context that includes register values of registers in the processor of a prior function executing on the processor in the constrained sensor device stored on a stack in memory to a different location in the memory, with the context including processor operating register values of the prior function, when a next function is identified as ready to run and the next function has a higher priority than the prior function executing on the constrained device.

8. The method of claim 7 wherein the processor executes a real-time operating system.

9. The method of claim 7 wherein scheduling periodically evaluates the functions not currently running to determine whether any of these are ready to run.

10. The method of claim 7 wherein an interrupt is used to determine that a function is ready to run by either a supplying of data to a pended function or a counting down of a timer event for a function that has suspended itself.

11. The method of claim 7 wherein the stack has functions stored according to respective priorities the method comprising:
determining whether the next function is ready to run and is of higher priority than the prior function and pushing next function data on top of the stack.

12. A constrained sensor device comprises: a processor device including registers;
random access memory in communication with the processor device;
a sensor element for sensing a physical condition, the sensor element sending data for processing to the processor device, with the processor device applying one or more user-defined independent executable functions to the data; and
a storage device storing a computer program product comprising instructions to cause the processor device to:
manage a dynamic set of the user-defined independent executable functions that are either built into a loaded image or downloaded during normal operation of the constrained sensor device to further cause the processor device to:
add a new function to a management structure that comprises an array or a linked list of function pointers;
update readiness and priority information in scheduler variables; and produce links between old and new code; and
schedule functions that are referenced through the management structure, to execute on the constrained sensor device, according to availability based on readiness information and priority of the scheduled functions relative to other functions obtained from the management structure, without saving context that includes register values of registers in the processor device of a prior function executing on the processor device in the constrained device stored on a stack in the memory to a different location in memory, with the context including processor operating register values of the prior function, when the scheduler identifies a next function that is ready to run and the next function has a higher priority than the prior function executing on the constrained device.

13. The device of claim 12 wherein the computer program product is a real-time operating system for execution on constrained sensor devices.

14. The device of claim 12 wherein the stack has functions stored according to respective priorities and when the next function is found ready to run that is of higher priority than the prior function, the next function pushes its data on top of the stack.

15. The device of claim 12 wherein the constrained device has less than 10 Kbytes of volatile memory.

16. The device of claim 12 wherein the constrained device is a device with less than a megabyte of flash/persistent memory and less than 20 Kbytes of RAM/volatile memory.

17. A networked detection system comprising:
a network of sensors and computing devices, with the network of sensors and computing devices comprising:
one or more constrained sensor devices with at least one of the constrained sensor devices comprising:
a first processing device;
a sensor element for sensing a physical condition, the sensor element sending data for processing to the first processing device, with the first processing device applying one or more user-defined independent executable functions to the data;
a storage device storing a computer program product comprising instructions to cause the first processor device to:
manage a dynamic set of the user-defined independent executable functions that are either built into a loaded image or downloaded during normal operation of the constrained sensor device, to further cause the first processing device to:

add a new function to a management structure that comprises an array or a linked list of function pointers;

update readiness and priority information in scheduler variables; and produce links between old and new code; and schedule functions that are referenced through the management structure to execute on the constrained sensor device according to availability based on readiness information and priority of the scheduled functions relative to other functions obtained from the management structure, without saving context that includes register values of registers in the first processing device of a prior function executing on the first processing device in the constrained device stored on a stack in the memory to a different location in the memory, with the context including processor operating register values of the prior function, when a next function is identified as ready to run and the next function has a higher priority than the prior function executing on the constrained device; and one or more fully functional sensor devices each comprising:

a second different type of processing device having greater processing capabilities than the first processing device;

second different memory coupled to the second different type of processing device; and a network connection to connect the one or more constrained sensor devices to the network.

* * * * *